United States Patent [19]

Bocek et al.

[11] Patent Number: 5,312,444
[45] Date of Patent: May 17, 1994

[54] CROSSPOINT SWITCH WITH IMPROVED DISCHARGE CONTROL FOR USE IN AN IMPLANTABLE DEFIBRILLATOR

[75] Inventors: Joseph M. Bocek, Seattle; Paul E. de Coriolis, Bellevue, both of Wash.

[73] Assignee: InControl, Inc., Redmond, Wash.

[21] Appl. No.: 91,213

[22] Filed: Jul. 13, 1993

Related U.S. Application Data

[63] Continuation-in-part of Ser. No. 902,998, Jun. 22, 1992, Pat. No. 5,251,624.

[51] Int. Cl.⁵ .................................................. A61N 1/39
[52] U.S. Cl. .................................................. 607/5
[58] Field of Search ................................. 607/4, 5, 6

[56] References Cited

U.S. PATENT DOCUMENTS

| | | | |
|---|---|---|---|
| 3,224,447 | 12/1965 | Becker et al. | 607/5 |
| 4,199,429 | 4/1993 | Kroll et al. | 607/5 |
| 5,044,367 | 9/1991 | Endres et al. | 607/5 |
| 5,083,562 | 1/1992 | de Coriolis et al. | |
| 5,111,816 | 5/1992 | Pless et al. | |
| 5,237,989 | 8/1993 | Morgan et al. | 607/5 |

*Primary Examiner*—William E. Kamm
*Assistant Examiner*—George Manuel
*Attorney, Agent, or Firm*—Foley & Lardner

[57] ABSTRACT

A pulse generator for use in a defibrillator provides cardioverting electrical energy to a heart through at least one lead having a pair of electrodes associated with the heart. Electrical energy is applied to the heart with a biphasic waveform having a first cardioverting phase and a second cardioverting phase. A crosspoint switch selectively couples a storage capacitor to the lead means. A master switch decouples the crosspoint switch from the storage capacitor while the crosspoint switch connections are changed between the first cardioverting phase and the second cardioverting phase. A control circuit provides independent control of the duration of both the first and second cardioverting phases.

46 Claims, 7 Drawing Sheets

CROSSPOINT SWITCH WITH IMPROVED DISCHARGE CONTROL FOR USE IN AN IMPLANTABLE DEFIBRILLATOR

CROSS REFERENCE TO RELATED APPLICATION

This application is a continuation in part of application Ser. No. 07/902,998, filed Jun. 22, 1992 now U.S. Pat. No. 5,251,624.

BACKGROUND OF THE INVENTION

The present invention generally relates to an automatic implantable atrial defibrillator for delivering cardioverting or defibrillating electrical energy to the atria of a human heart. The present invention is more particularly directed to a crosspoint switch for use in an automatic implantable atrial defibrillator which provides cardioverting or defibrillating electrical energy. The invention also provides improved discharge control when supplying defibrillating electrical energy having a biphasic waveform to the atria of the heart.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators has become a commercial reality.

Implantable atrial defibrillators proposed in the past have exhibited a number of disadvantages which probably has been the cause of these defibrillators from becoming a commercial reality. Two such defibrillators, although represented as being implantable, were not fully automatic, requiring human interaction for cardioverting or defibrillating the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

An implantable defibrillator must be powered by a portable, depletable power source, such as a battery. It has been long believed that as much electrical energy is required to cardiovert or defibrillate the atria of the heart as is required to cardiovert or defibrillate the ventricles of the heart, on the order of ten joules or more. In addition, episodes of atrial fibrillation occur much more frequently than do episodes of ventricular fibrillation. As a result, due to the contemplated required cardioverting or defibrillating energy levels for cardioverting or defibrillating the atria of the heart and the predicted required frequency of delivering such energies, it has long been believed that an implantable atrial defibrillator would deplete its power source so rapidly that frequent battery replacement would be required. Since battery replacement would require the surgical implanting of the defibrillator, it has long been believed that an implantable atrial defibrillator could not be a commercial reality. To this day, a commercially implantable atrial defibrillator remains unavailable.

Defibrillators generally include a means, such as a storage capacitor, for storing the electrical energy required to cardiovert or defibrillate the heart. A charging circuit is provided for charging the storage capacitor to a potential of several hundred volts. Control circuitry is further provided to detect the level of charge stored on the storage capacitor and to control the discharge of the capacitor through lead means to the heart.

Implantable defibrillators are known in the art which deliver cardioverting or defibrillating electrical energy from the storage capacitor with a biphasic waveform. With such a biphasic waveform, the cardioverting or defibrillating electrical energy is initially applied with a first polarity, and then with a second and reversed polarity in rapid succession. The electrical energy is applied through lead means having at least two electrodes in electrical contact with the heart.

A crosspoint switch is generally utilized for supplying the biphasic electrical energy from a single storage capacitor. The crosspoint switch may be configured to first couple a positive terminal of the storage capacitor to a first electrode and a negative terminal of the storage capacitor to a second electrode during a first cardioverting phase of the biphasic waveform and to couple the positive terminal of the storage capacitor to the second electrode and the negative terminal of the storage capacitor to a first electrode during a second cardioverting phase of the biphasic waveform Crosspoint switches exhibit a distinct advantage because they conserve space within an implantable defibrillator by eliminating the need for a second storage capacitor with reverse polarity and its associated charging circuit.

One concern in implementing a crosspoint switch for delivering cardioverting electrical energy with a biphasic waveform is inadvertently shorting out the storage capacitor between the first cardioverting phase and the second cardioverting phase. This can occur during switching if both terminals of the storage capacitor are coupled to the same electrode, even briefly. If this occurs, the shorted capacitor could lose all and most assuredly a significant portion of its stored electrical energy.

To reduce the risk of shorting out the storage capacitor, crosspoint switches have been associated with control circuits which verify that the connections within the switch for the first cardioverting phase are broken before completing the connections for the second cardioverting phase. To provide this verification, such control circuits have had to be rather elaborate to introduce switching delays to prevent the storage capacitor from being shorted out.

In addition to being rather elaborate, prior crosspoint switch control circuits have exhibited the further disadvantage of lacking the ability to adequately control the durations of the first and second cardioverting phases. Such phase duration control is desirable for tailoring the applied electrical therapy to a patient's particular condition. Ideally, the duration of both the first and the second cardioverting phases should be independently controllable from a zero time duration (analogous to a monophasic waveform) to a predetermined maximum time duration. Previous crosspoint switch control circuits have lacked this flexibility. The crosspoint switch and control circuit of the present invention overcomes these shortcomings of earlier devices. The crosspoint switch and control circuit of the present invention provides for decoupling the storage capacitor from the lead means while the crosspoint switch connections are changed. The present invention also provides independent control of the duration of each cardioverting phase. As disclosed herein, first and second digital counters are provided for controlling the duration of the first and second cardioverting phases, respectively. Other features and advantages of the present invention shall become apparent hereinafter.

SUMMARY OF THE INVENTION

The invention therefore provides an improved pulse generator for providing cardioverting electrical energy to the heart through lead means. The pulse generator includes a depletable, low voltage power source, a storage capacitor having a positive terminal and a negative terminal for providing the cardioverting electrical energy, and charging means for converting the low voltage of the power source to a pulsating high voltage for charging the storage capacitor. The improvement comprises coupling means for selectively coupling the storage capacitor to the lead means with a first polarity for applying a first portion of the cardioverting electrical energy through the lead means to the heart during a first cardioverting phase, and with a second polarity reversed from the first polarity for applying a second portion of the cardioverting electrical energy through the lead means to the heart during a second cardioverting phase. Master switch means selectively decouple the storage capacitor from the lead means between the first and second cardioverting phases.

The invention also provides a method for providing electrical energy stored in a storage capacitor having a positive terminal and a negative terminal through lead means having a first electrode and a second electrode for conveying the electrical energy to the heart. The method includes the steps of applying a first portion of the electrical energy with a first polarity through the lead means to the heart during a first cardioverting phase, applying a second portion of the electrical energy with a second polarity through the lead means to the heart during a second cardioverting phase, the second polarity being opposite the first polarity, and decoupling the lead means from the storage capacitor between the first and second cardioverting phases.

The invention still further provides a crosspoint switch control circuit for controlling a crosspoint switch and a master switch for use in a defibrillator for providing cardioverting electrical energy to a heart through lead means having first and second electrodes for providing cardioverting electrical energy to the heart from a storage capacitor having a positive and a negative terminal, the crosspoint switch being responsive to a first control signal for coupling the positive terminal to the first electrode and the negative terminal to the second electrode and responsive to a second control signal for coupling the positive terminal to the second electrode and the negative terminal to the first electrode, the master switch being responsive to a shock control signal for decoupling the storage capacitor from the lead means. The control circuit includes phase control means coupled to the crosspoint switch for generating the first and second control signals. The control circuit further includes duration control means for controlling the phase control means and generating the shock control signal to cause the master switch to decouple the storage capacitor from the lead means between the first and second cardioverting phases.

BRIEF DESCRIPTION OF THE PREFERRED EMBODIMENTS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION OF THE PREFERRED EMBODIMENTS

Figure 1:
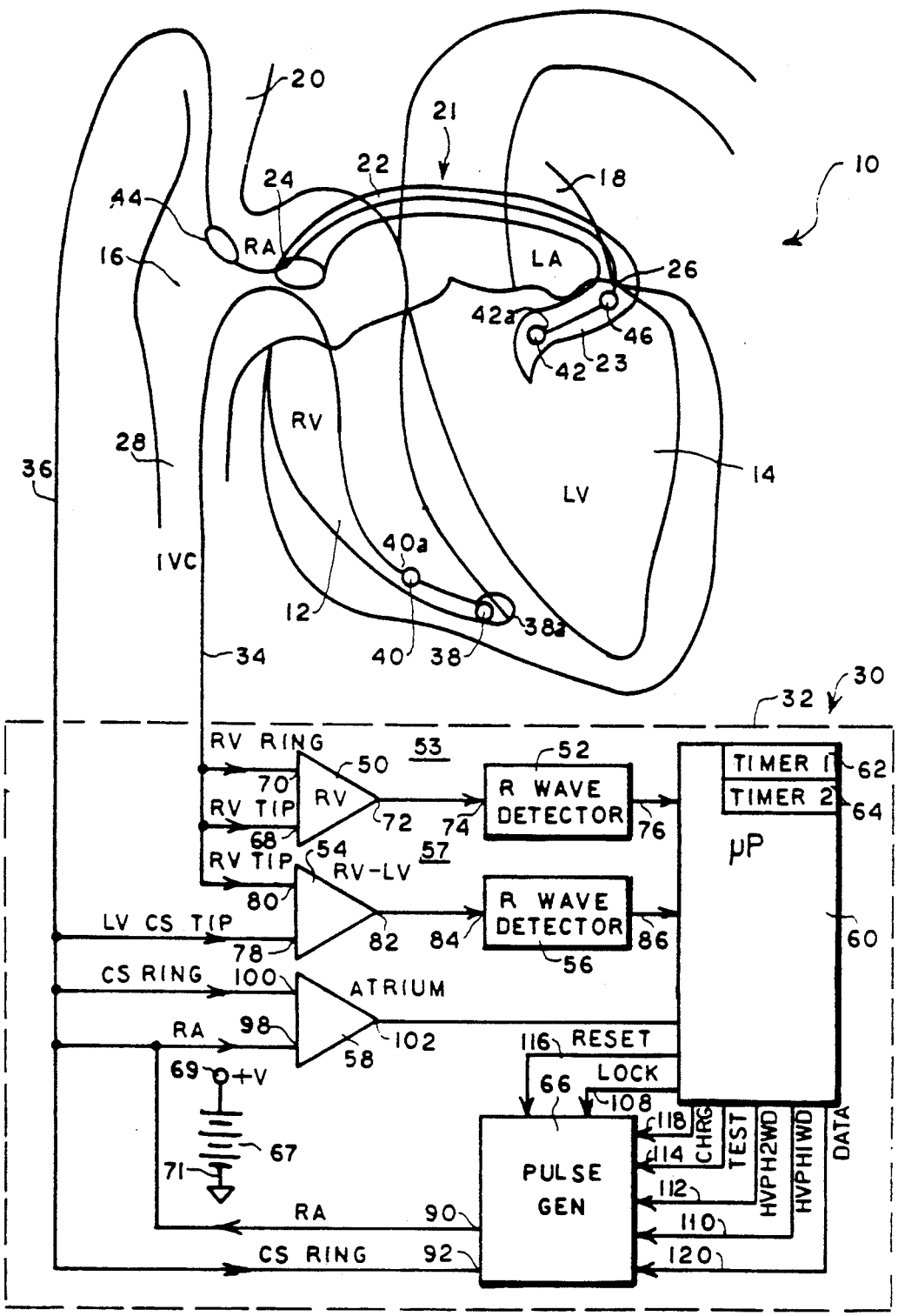
FIG. 1 is a schematic block diagram of a fully implantable atrial defibrillator embodying the present invention.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary channel 21 which includes the coronary sinus 22 and the great cardiac vein 23, the coronary sinus ostium or opening 24, the left ventricular free wall 26, and the inferior vena cava 28. In addition, as used herein, the term "depolarization activation waves" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of depolarization activation waves in the right ventricle between a first pair of locations 38a and 40a within the right ventricle 12. As illustrated, the lead 34 is fed through the inferior vena cava 28, into the right atrium 16, and then into the right ventricle 12. As will be appreciated by those skilled in the art, a second path for lead 34 could alternatively be through the superior vena cava 20, into the right atrium 16, and then into the right ventricle 12.

The second lead 36 generally includes a first or distal electrode 42, a second or ring electrode 46, and a third electrode 44. As illustrated, the second lead 36 is flexible and arranged to be passed down the superior vena cava 20, into the right atrium 16, into the coronary sinus ostium 24, advanced into the coronary sinus 22 and great cardiac vein 23 of the heart near the left side thereof so that the first or distal electrode 42 is within the great vein 23 of the heart adjacent the left ventricle 14. The electrodes 42, 44, and 46 are spaced apart such that when the first electrode 42 is within the great cardiac vein 23 adjacent the left ventricle 14, the second electrode 46 is within the great vein 23 or coronary sinus 22 beneath the left atrium 18 near the left ventricle 14 and the third electrode 44 is within the right atrium 16.

The first electrode 42 of the second lead 36 and the electrode 38 of the first lead 34 permit bi-polar sensing of depolarization activation waves between a second pair of locations 38a and 42a of the heart. Alternatively, the second pair of electrodes may include electrodes 42 and 40 and, as a result, the second pair of locations may be locations 42a and 40a. As will be noted in FIG. 1, the spacing between the second pair of locations 38a and 42a is greater than the spacing between the first pair of locations 38a and 40a. These relative spacings between the first and second pairs of locations between which depolarization activation waves are sensed enable reliable detection of depolarization activation waves.

The second electrode 44 together with the third electrode 46 of the second lead 36 provide for the delivery of defibrillating or cardioverting electrical energy to the atria. Because the second electrode 46 is located beneath the left atrium 18 near the left ventricle 14 and the third electrode 46 is within the right atrium 16, the electrical energy applied between these electrodes will be substantially confined to the atria 16 and 18 of the heart 10. Hence, the lead 36 forms a lead means associated with the atria 16 and 18 of the heart 10 for applying the defibrillating or cardioverting electrical energy to the heart.

Within the enclosure 32, the atrial defibrillator 30 includes a first sense amplifier 50, a first R wave detector 52, a second sense amplifier 54, a second R wave detector 56 and a third sense amplifier 58. Within the enclosure 32, the atrial defibrillator 30 also includes a microprocessor 60, a pulse generator 66, and a depletable, low voltage, power source or battery 67. The battery 67 includes a negative terminal 71 which may be coupled to the various internal components of the defibrillator 30 and a positive terminal 69 coupled to common potential. The battery 67 provides power to the various components at a low voltage of, for example, three volts.

The first sense amplifier 50 includes a first input 68 which is coupled to electrode 38 of the first lead 34 and a second input 70 which is coupled to electrode 40 of the first lead 34. The first sense amplifier 50 thus senses the electrical activity of the heart 10 between the first pair of locations of the heart 38a and 40a. It amplifies the sensed electrical activity of the heart and provides at an output 72 an amplified signal or first electrocardiogram representative of the electrical activity of the heart sensed by the bi-polar electrodes 38 and 40.

The first R wave detector 52 includes an input 74 which is coupled to the output 72 of the first amplifier 50. The R wave detector 52 includes a threshold detecting means or circuit which provides a substantially constant first electrical output having a duration substantially equal to the duration of the depolarization activation waves (R waves) sensed between electrodes 38 and 40. As a result, the electrodes 38 and 40 and the first sense amplifier 50 form a first sensing means 53 for sensing electrical activity of the heart including depolarization activation waves between the first pair of spaced apart locations of the heart 38a and 40a. The first R wave detector 52 forms a first output means for isolating the R wave feature of the first electrocardiogram and for producing a first electrical output, at output 76, having a first predetermined characteristic or duration corresponding and substantially equal to the duration of the depolarization activation waves (R waves) sensed between the first pair or locations of the heart 38a and 40a.

The second sense amplifier 54 includes a first input 78 which is coupled to the electrode 42 of the second lead 36 and a second input 80 which is coupled to electrode 38 of the first lead 34. As a result, the second sense amplifier 54 senses the electrical activity of the heart between the second pair of locations of the heart 38a and 42a. It provides at an output 82 an amplified signal or second electrocardiogram representative of the electrical activity of the heart sensed between the second pair of locations of the heart 38a and 42a.

The second R wave detector 56 includes an input 84 for receiving the amplified signal provided from the output 82 of the second sense amplifier 54. The second R wave detector 56 also includes a second threshold detecting means or circuit for providing a substantially constant second electrical output at output 86 having a duration substantially equal to the duration of the depolarization activation waves sensed by the second sense amplifier 54. As a result, electrode 42, electrode 38, and sense amplifier 54 form a second sensing means 57 for sensing electrical activity of the heart including depolarization activation waves between the second pair of locations of the heart 38a and 42a. The second R wave detector 56 forms a second output means for isolating the R wave feature of the second electrocardiogram for producing a second electrical output having a second predetermined characteristic or duration corresponding and substantially equal to the duration of the depolarization activation waves (R waves) sensed between the second pair of locations of the heart 38a and 42a.

A first timer 62 of microprocessor 60 times the duration of the first electrical output of the first electrical output provided by the first R wave detector 52 for timing the duration of a depolarization activation wave (R wave) sensed between the first pair of locations 38a and 40a. A second timer 64 of microprocessor 60 also times the duration of the second electrical output provided by the second R wave detector 56 for timing the duration of the same depolarization activation wave (R wave) sensed between the second pair of locations 42a and 38a. Since the spacing between the second pair of locations 42a and 38a is greater than the spacing between the first pair of locations 40a and 38a, if the electrical activity of the heart sensed by the first sensing means 53 and second sensing means 57 is a true depolarization activation wave (R wave), the duration of the second electrical output provided by R wave detector 56 will be longer than the duration of the first electrical output provided by the first R wave detector 52. Hence, the predetermined features (R waves) of the first and second electrocardiograms and more specifically, the first and second predetermined characteristics (durations) of those features will be different.

The microprocessor 60 reliably detects a depolarization activation wave when the second electrical output has a duration which is longer than the duration of the first electrical output. If the electrical activity of the heart sensed by the first and second sensing means 53 and 57 respectively is noise, the duration of the first and second electrical outputs will be substantially the same. Hence, in the foregoing manner, the atrial defibrillator 30 reliably detects electrical activations (R waves) of the heart 10, even in an environment of electrical noise.

As described in copending U.S. application Ser. No. 07/685,130, filed Apr. 12, 1991, in the names of John M. Adams and Clifton A. Alferness and entitled ATRIAL DEFIBRILLATOR AND METHOD, which application is assigned to the assignee of the present invention and incorporated herein by reference, the microprocessor 60 utilizes the intervals between the detected R waves to determine if atrial fibrillation might be present. If such criteria are met, the microprocessor 60 activates the third sense amplifier 58 for sensing electrical activity in the atria 16 and 18 of the heart 10. To that end, the third sense amplifier 58 includes a first input 98 which is coupled to electrode 46 and a second input 100 which is coupled to electrode 44. The third sense amplifier 58 includes an output 102 which is coupled to the microprocessor 60 for providing the microprocessor 60 with an amplified signal representing the electrical activity of the atria 16 and 18 of the heart.

The microprocessor 60, as described in the aforementioned copending U.S. application Ser. No. 07/685,130, digitizes the amplified electrical signal provided by the third sense amplifier 58 and processes the digitized values of the atrial activity for detecting and confirming the presence of atrial fibrillation. Such atrial fibrillation detection may be implemented by the microprocessor 60 as described in the aforementioned copending application. Alternatively, the microprocessor 60 may be implemented in accordance with the atrial fibrillation detection algorithms disclosed in a paper: Janice Jenkins, Ki Hong Noh, Alain Guezennec, Thomas Bump, and Robert Arzbaecher, "Diagnosis of Atrial Fibrillation Using Electrograms from Chronic Leads: Evaluation of Computer Algorithms," *PACE*, Vol. 11, pp. 622-631, May 1988. Implementing such algorithms by a microprocessor such as microprocessor 60 is well within the purview of one skilled in the art.

As described in copending U.S. application Ser. No. 07/902,998, filed Jun. 22, 1992, in the names of Joseph M. Bocek, Kenneth Ross Infinger and Darrell O. Wagner and entitled PULSE GENERATOR FOR USE IN AN IMPLANTABLE ATRIAL DEFIBRILLATOR, the pulse generator 66 stores electrical energy within a storage capacitor and discharges the storage capacitor to apply cardioverting or defibrillating electrical energy to the heart.

The pulse generator 66 is coupled to the microprocessor 60 over a plurality of control lines 108, 110, 112, 114, 116 and 118 and a multiple-bit data bus 120. The pulse generator 66 includes a first output 90 which is coupled to electrode 46 of lead 36 and a second output 92 coupled to electrode 44 of lead 36. As will be seen hereinafter, the pulse generator 66 is responsive to control signals received over the control lines 108, 110, 112, 114, 116 and 118 to store cardioverting or defibrillating electrical energy within a storage capacitor. Once the storage capacitor has been charged to a desired level, the pulse generator 66 responsive to control signals received over lines 108, 110, 112, and 116, discharges the storage capacitor from outputs 90 and 92 to apply cardioverting or defibrillating electrical energy to the electrodes 46 and 44. As will be seen further hereinafter, the pulse generator 66 includes a crosspoint switch which is operable for applying the cardioverting or defibrillating electrical energy to electrodes 46 and 44 with a biphasic waveform having first and second cardioverting phases. In the first phase, electrode 46 is made positive with respect to electrode 44 and in the second phase, electrode 44 is made positive with respect to electrode 46. In addition, the duration of the first and second phases of the biphasic waveform are independently controllable.

Control line 118 conducts a charge control signal to the pulse generator 66 to cause a charging circuit within pulse generator 66 to store the electrical energy within the storage capacitor. Control lines 108 and 116 conduct a reset signal and a lock signal to the pulse generator to reset portions of the pulse generator to a predetermined initial state. Control lines 110 and 112 conduct control signals to the pulse generator 6 for controlling the duration of the cardioverting or defibrillating electrical energy to outputs 90 and 92 in accordance with the aforementioned biphasic waveform. Lastly, control line 114 conducts a test control signal to the pulse generator 66 to cause the pulse generator 66 to discharge the storage capacitor internally within the pulse generator 66 for test purposes. Such testing may also be performed at periodic intervals for reforming the dielectric of the internal storage capacitor of the pulse generator 66

Figure 2:
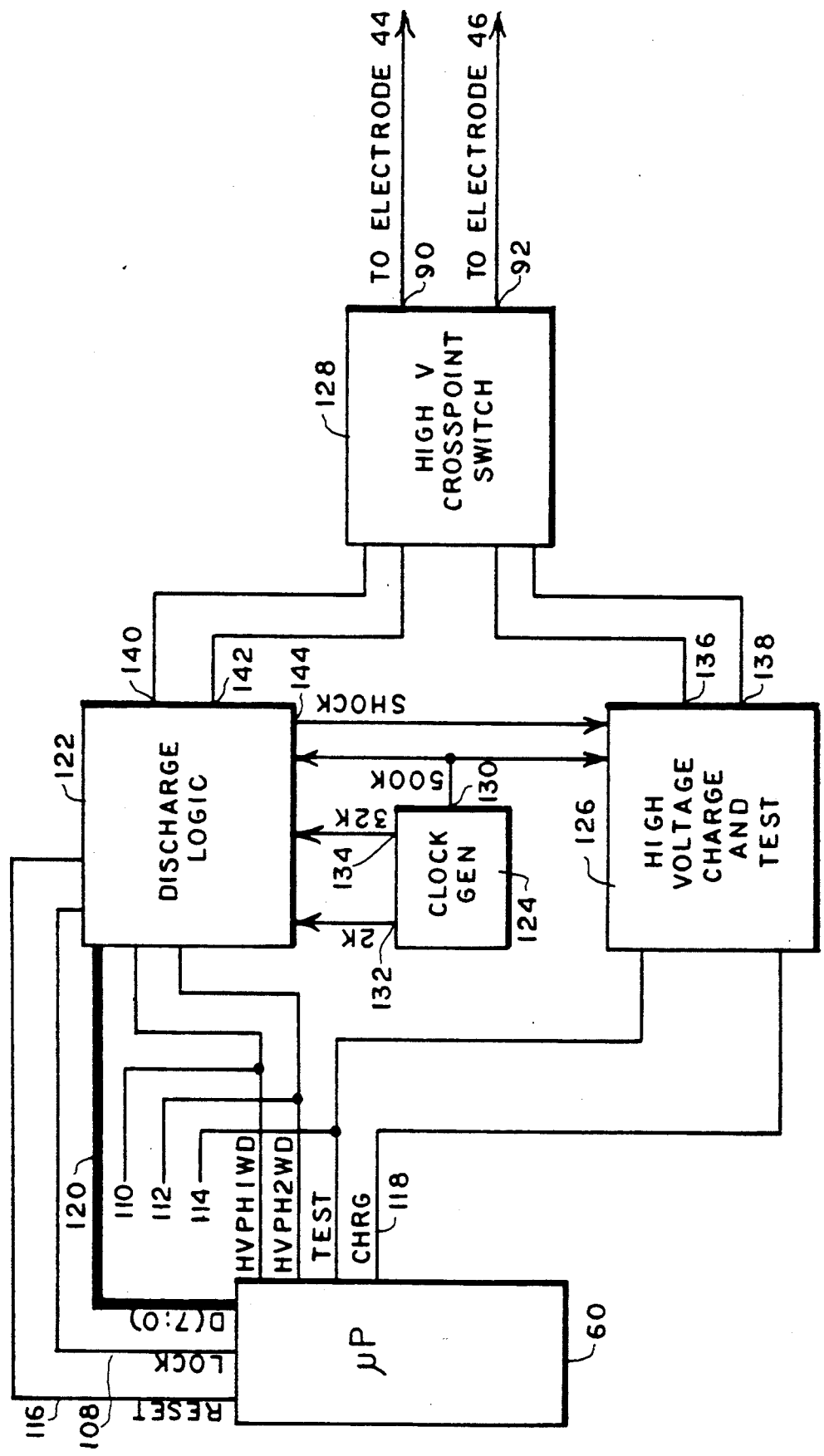
FIG. 2 is a block diagram of the pulse generator of the atrial defibrillator of FIG. 2 embodying the present invention.

Referring now to FIG. 2, it illustrates, in block diagram form, the pulse generator 66 of FIG. I in conjunction with the microprocessor 60. The pulse generator 66 generally includes discharge logic 122, a clock generator 124, a high voltage charge and test circuit 126 and a crosspoint switch circuit 128.

Control line 118 is coupled to the high voltage charge and test circuit 126. Control lines 116 and 108 are coupled to the discharge logic 122. Control line 114 is coupled to the high voltage charge and test circuit 126. Lastly, control lines 110 and 112 are coupled to the discharge logic 122.

Clock generator 124 includes an output 130 which is coupled to discharge logic 122 and the high voltage charge and test circuit 126. Clock generator 124 also includes outputs 132 and 134 which are coupled to the discharge logic 122. The high voltage charge and test circuit 126 includes a first output 136 and a second output 138 which are coupled to the high voltage crosspoint switch circuit 128. The output 136 is coupled to the positive terminal of the storage capacitor and the second output 138 is coupled to the negative terminal of the storage capacitor when the aforementioned master switch is closed under control of discharge logic 122. This allows the storage capacitor to be coupled to the high voltage crosspoint switch circuit 128 for application of the cardioverting or defibrillating electrical energy to electrodes 44 and 46 from outputs 90 and 92.

The discharge logic 122 includes a first output 140, a second output 142, and a third output 144. The outputs 140 and 142 are coupled to the high voltage crosspoint switch 128. The output 144 is coupled to the high voltage charge and test circuit 126. When the cardioverting or defibrillating electrical energy is applied to the electrodes 46 and 44 during the first phase, the first output 140 of discharge logic 122 is active and during the second phase output 14 is active. During both the first and second phases, output 144 is active to cause the aforementioned master switch to close and couple the storage capacitor to the crosspoint switch. The high voltage crosspoint switch circuit 128 and the high voltage charge and test circuit 126 therefore applies the cardioverting or defibrillating electrical energy stored, in, the storage capacitor of the high voltage charge and test circuit 126 responsive to the enable control signals provided at outputs 140, 142 and 144 of the discharge logic 122.

For applying the cardioverting or defibrillating electrical energy to the electrodes 46 and 44, the high voltage crosspoint switch circuit 128 includes the aforementioned first pulse generator output 90 and the second pulse generator output 92. As illustrated, these outputs are coupled to the electrodes 46 and 44 respectively.

Figure 3A:
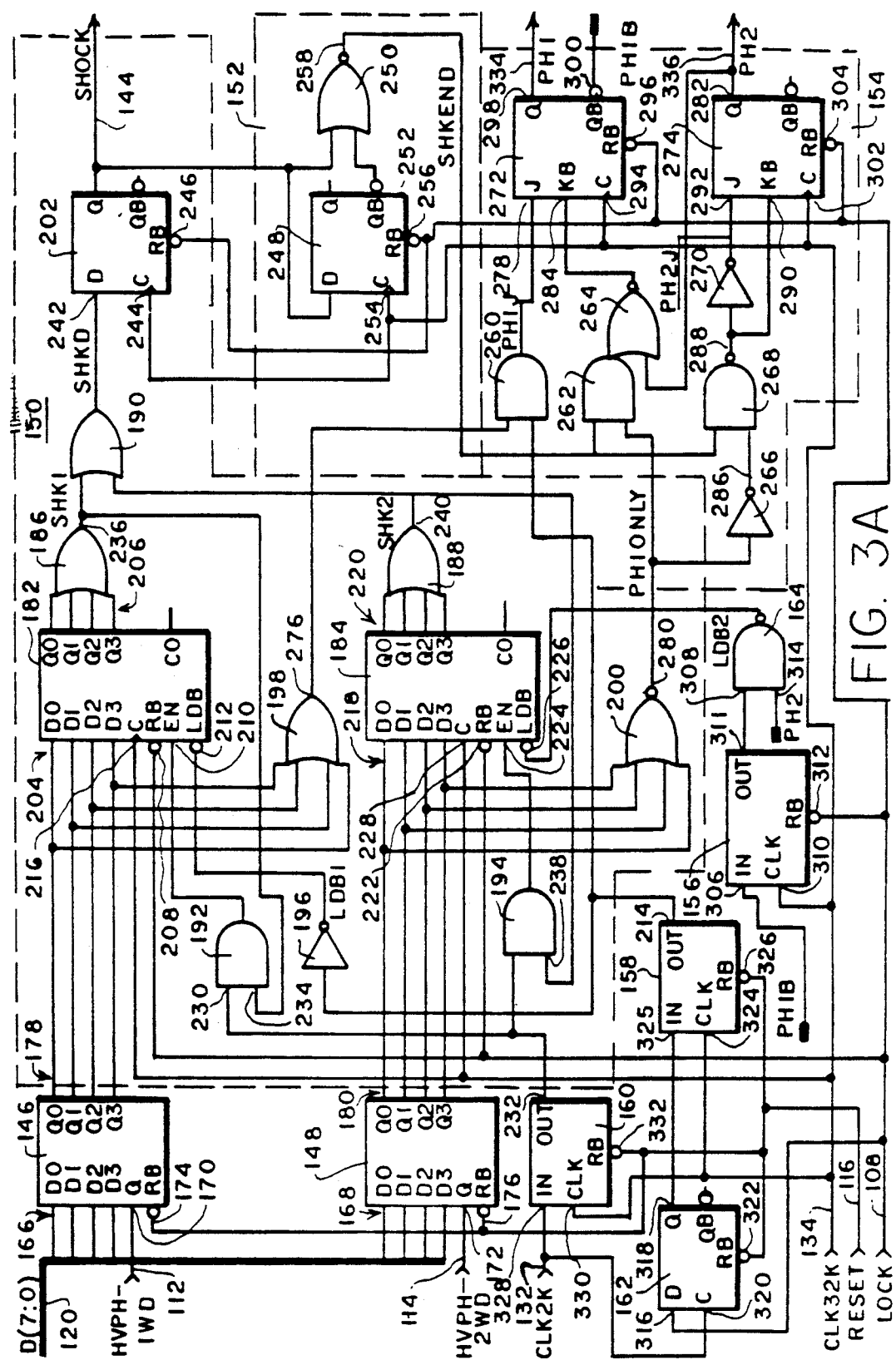
FIGS. 3A and 3B are a schematic diagram of the discharge logic circuit of FIG. 2 embodying aspects of the present invention.

Referring now to FIG. 3A, it illustrates, in schematic diagram form, a portion of the discharge logic circuit 122 of FIG. 2. As previously mentioned, when the cardioverting or defibrillating electrical energy is applied to the atria of the heart through the lead 36 and electrodes 46 and 44, the electrical energy is preferably applied with a biphasic waveform wherein electrode 46 is positive with respect to electrode 44 during a first phase and electrode 44 is positive with respect to electrode 46 during an immediately subsequent second phase. Preferably, the first and second phases are equal in duration of 3 milliseconds. At all times other than when the cardioverting or defibrillating electrical energy is to be applied to the heart, the microprocessor 60 holds the discharge logic 122 in an inactive or reset state, by holding the LOCK signal 108 active low. When the cardioverting or defibrillating electrical energy is applied to electrodes 46 and 44 for cardioverting or defibrillating the atria of the heart, the microprocessor first sets the desired duration of each discharge phase by supplying four bit binary values over data bus 120 to the discharge control logic 122 and latches the four bit values with signals on control lines 112 and 114. The microprocessor 60 then sets control line LOCK high, to release the discharge control logic from a reset condition. The discharge control logic 122 of FIGS. 3A and 3B then operates to generate constant level phase one and phase two control signals and to convert the constant level phase one and phase two control signals to time varying periodic phase one and phase two drive signals at outputs 140 and 142 for controlling the crosspoint switch circuit 128 of FIG. 2. The discharge control logic 122 of FIGS. 3A and 3B further operates to generate a constant shock control signal at output 144. As will be discussed in conjunction with FIG. 4, the high voltage charge and test circuit 126 converts the constant shock control signal to a time varying periodic shock control drive signal for controlling the aforementioned master switch for coupling the storage capacitor to the high voltage crosspoint switch 128.

As shown in FIG. 3A, discharge logic circuit 122 includes latches 146 and 148, duration control means 150, edge detect means 152, phase control means 154, positive edge detectors 156, 158 and 160, latch 162, and NAND gate 164.

The latches 146 and 148 are preferably four bit latches and have inputs 166 and 168, respectively, coupled to the four least significant bits D3, D2, D1 and D0 of the data bus 120, coupled to microprocessor 60 (FIG. 1). The latch 146 includes a clock input 170 coupled to control line 112 which conveys a signal HVPH1WD from the microprocessor 60. The latch 148 includes a clock input 172 coupled to control line 114 Which conveys a signal HVPH2WD from microprocessor 60. Latch 146 includes a reset input 174 and latch 146 includes a reset input 176. Both reset inputs 174 and 176 are coupled to control line 116 which conveys a reset signal from the microprocessor 60. The latch 146 has a four bit output 178 coupled to the duration control means 150. Latch 148 also has a four bit output 180 coupled to the duration control means 150.

The duration control means 150 includes a first counter 182, a second counter 184, a first OR gate 186, a second OR gate 188, a third OR gate 190, a first AND gate 192, a second AND gate 194, an inverter 196, a fourth OR gate 198, a NOR gate 200 and a latch 202. The first counter 182 includes a four bit input 204 coupled to the four bit output 178 of latch 146 and a four bit output 206 coupled to the four inputs of the first OR gate 186. The first counter 182 further includes a reset input 208 coupled to control LOCK signal 108 which conveys a shock disable signal from microprocessor 60. The first counter further includes an enable input 210 coupled to the output of the first AND gate 192, and a load input 212 coupled to the output of the inverter 196. The input of the inverter 196 is coupled to the output 214 of a positive edge detector 158. The first counter 182 lastly includes a clock input 216 coupled to the clock signal on line 134 (FIG. 2).

The second counter 184 includes a four bit input 218 coupled to the four bit output 180 of latch 148 and a four bit output 220 coupled to the inputs of second OR gate 188. The second counter 184 further includes a reset input 222 coupled to the control signal 108, an enable input 224 coupled to the output of the second AND gate 194, a load input 226 coupled to the output of NAND gate 164, and a clock input 228 coupled to the clock signal on line 134.

The AND gate 192 has a first input 230 coupled to the output 232 of positive edge detector 160 and a second input 234 coupled to the output 236 of OR gate 186. The OR gate 198 has four inputs coupled to the four bit output 178 of latch 146. The AND gate 194 has a first input coupled to the output 232 of positive edge detector 160 and a second input 238 coupled to the output 240 of OR gate 188. NOR gate 200 has four inputs coupled to the four bit output 180 of latch 148.

The OR gate 190 has a first input coupled to the output 236 of the OR gate 186 and a second input coupled to the output 240 of the OR gate 188. The latch 202 has a data input 242 coupled to the output of the OR gate 190 and an output coupled to the shock control signal on line 144 of the discharge logic circuit 122. The latch 202 also has a clock input 244 coupled to the clock line 134 and a reset input 246 coupled to control line 108.

The edge detect means 152 includes a latch 248 and a NOR gate 250. The latch 248 has an input coupled to the shock control signal on line 144 and an inverting output 252 coupled to a first input of the NOR gate 250. The latch 248 also has a clock input 254 coupled to the clock line 134 and a reset input 256 coupled to the control line 108. The NOR gate 250 has a second input coupled to the shock control signal on line 144 and an output 258.

The phase control means 154 includes a first AND gate 260, a second AND gate 262, a NOR gate 264, a first inverter 266, a NAND gate 268, a second inverter 270, a first JK flip flop 272 and a second JK flip flop 274. The AND gate 260 has a first input coupled to the output 276 of the OR gate 198, a second input coupled to the output 214 of the positive edge detector 158, and an output coupled to the J input 278 of JK flip flop 272. The second NAND gate 262 has a first input coupled to the output 258 of the NOR gate 250, a second input coupled to the output 280 of the NOR gate 200, and an output coupled to a first input of the NOR gate 264. The NOR gate 264 has a second input coupled to the output 282 of the second JK flip flop 274 and an output coupled to the $\overline{K}$ input 284 of the first JK flip flop 272.

The inverter 266 has an input coupled to the output 280 of NOR gate 200 and an output 286 coupled to a first input of the NAND gate 268. The NAND gate 268 has a second input coupled to the output 258 of NOR gate 250, and an output 288 coupled to both the input of the inverter 270 and the $\overline{K}$ input 290 of the second JK flip flop 274. The output of the inverter 270 is coupled to the J input 292 of the second JK flip flop 274.

The first JK flip flop 272 has a clock input 294 coupled to the clock line 134, a reset input 296 coupled to control line 108, an output 298 and an inverting output 300. The second JK flip flop 274 has a clock input 302 coupled to the 15 clock line 134 and a reset input 304. The first JK flip flop 272 provides a constant first phase control signal at its output 298 to line 334. The second JK flip flop 274 provides a constant second phase control signal at its output 282 to line 336.

The inverting output 300 of the first JK flip flop 272 is coupled to the input 306 of the positive edge detector 156. The output 311 of the positive edge detector 156 is coupled to a first input 308 of the NAND gate 164. The positive edge detector 156 also has a clock input 310 coupled to the clock line 134 and a reset input 312 coupled to the control line 108. The NAND gate 164 has a second input 314 coupled to the output 282 of the second JK flip flop 274.

The latch 162 has an input 316 coupled to the control line 108 and an output 318 coupled to the input of the positive edge detector 158. The latch 162 further has a clock input 320 coupled to clock line 132 and a reset input 322 coupled to control line 116. The positive edge detector 158 has an input 325, a clock input 324 coupled to clock line 134 and a reset input 326 coupled to the control line 116. The positive edge detector 160 has an input 328 coupled to clock line 132, a clock input 330 coupled to clock line 134, and a reset input 332 coupled to control line 116.

The operation of the discharge logic circuit 130 begins at system reset with assertion of the control lines 116 and 108 to reset to a known, predetermined state the latches 146 and 148, the counters 182 and 184, the latches 248, 202 and 162, the first and second JK flip flops 272 and 274, and the positive edge detectors 156, 158, 160 and 162. Assertion of the control lines 116 and 108 causes the respective outputs of these circuit elements to assume a logic 0, or inactive, level.

The microprocessor 60 (FIG. 2) supplies to the discharge logic circuit 122 a four bit value on the data bus 120. The four bit value corresponds to the duration of the cardioverting electrical energy applied to the heart in a manner to be discussed below. The microprocessor 60 supplies over the data bus 120 a four bit value corresponding to the duration of a first cardioverting phase and asserts the HVPD1WD control signal on control line 112 to load the four least significant bits of the data bus 120 into the latch 146. Similarly, the microprocessor 60 supplies over data bus 120 a four bit value corresponding to the duration of a second cardioverting phase and asserts HVPH2WD control signal 114 to load the four least significant bits of the data bus 120 into the latch 148.

The counters 182 and 184 of the duration control means 160 operate as follows. When an active low signal is asserted at load inputs 212 and 226 of counters 182 and 184 respectively, the four bits of data present at the four bit inputs 204 and 218 of each respective counter 182 and 184 are latched into each respective counter 182 and 184. While the enable inputs 210 and 224 respectively of counters 182 and 184 are held in a logic 0 state, the counters merely latch the data, providing the data to the outputs 206 and 220 respectively of each counter. When the enable inputs 210 and 224 are supplied with a logic high level, counting is enabled. Responsive to clock signals supplied to clock inputs 216 and 228, respectively, counters 182 and 188 count down, decrementing the four bit output by 1 in response to each received clock pulse.

Thus, the four bits of data latched into latch 146 are loaded into counter 182 when an active low load signal is asserted at input 212. Input 212 will receive a low signal when the input to inverter 196 is high. The input to inverter 196 is controlled by the positive edge detector 158.

The positive edge detectors 156, 158 and 160 function as follows. In response to a reset signal received at reset inputs 312, 326 and 332, respectively, the outputs of the positive edge detectors 156, 158 and 160 are reset to a logic 0 level. So long as the signal applied to inputs 306, 325 and 328, respectively, remains at a logic 0 level, the output of positive edge detectors 156, 158 and 160 will remain low. When the signal applied to the inputs 306, 325 and 328 moves from a logic 0 level to a logic 1 level, corresponding to a positive edge, the output 311, 214 or 232, respectively, changes to a high logic level upon the next rising edge of the clock signal applied to the clock input 310, 324 or 330, respectively. Thus, the output of the positive edge detector only changes in response to a received positive edge and only for a duration equal to the duration of the input clock pulse.

Therefore, the counter 182 will be loaded when the output 214 of positive edge detector 158 changes to a logic 1 level. This will occur when the clock signal 134 clocks in a logic 1 level from the output 318 of the latch 162. This, in turn, will occur when the latch 162 latches a logic 1 level at input 316 in response to a clock signal received at clock input 320. The input 316 will receive a logic 1 level following the removal of the active low LOCK signal on control line 108. The clock input 320 of latch 162 is clocked by the clock signal 132.

Preferably, the clock signal on the clock line 132 is a 50% duty cycle signal having a frequency of 2K or 2048 Hz. Further, the clock signal on the clock line 134 preferably is a 50% duty cycle clock signal having a frequency substantially equal to 32K or 32,768 Hz.

As can be seen then, following assertion of the LOCK signal 108 and the reset signal 116 to perform the initial reset of the discharge control logic 122, the LOCK signal 108 is deasserted to a logic 1 level which is then clocked into the latch 162 by a 2K clock signal on clock line 132. Latching a high level into the latch 162 produces a logic 1 output on the output 318. This logic 1 output is detected by the positive edge detector 158 In response to the next received 32K clock pulse on clock line 134, the positive edge detector 158 provides to the output 214 a single positive pulse of duration substantially equal to the received 32K clock pulse. This positive pulse provided to the output 214 is inverted by the inverter 196, which provides a negative pulse to the input 212 of the counter 182. This received negative pulse causes the data on the output 178 of the latch 146 to be loaded into the counter 182 and be presented at the four bit output 206 of the counter 182.

As noted above, counters 182 and 184 preferably count down in response to a received clock signal at clock inputs 216 and 228 when a logic 1 level is supplied to the enable inputs 210 and 224, respectively. In response to a received 2K clock pulse on the clock line 132, the positive edge detector 160 will provide to the output 232 a positive pulse substantially equal in duration to a 32K clock pulse received on the clock line 134 at the input 330. The positive pulse at the output 232 will be coupled through the AND gates 192 and 194 to the enable inputs 210 and 224 of counters 182 and 184, respectively. Thus, the counting of the counters 182 and 184 is in effect clocked by the 2K clock signal on clock line 132.

The AND gate 192 has a second input 234 coupled to the output 236 of the OR gate 186. Similarly, the AND gate 194 has a second input 238 coupled to the output 240 of the OR gate 188. The output 236 of the OR gate 186 will be high whenever one or more of the outputs of the four bit output 206 of the counter 182 is high. Thus, the AND gate 192 acts to decouple the enable input 210 of the counter 182 from clocking signals applied to the input 230 of the AND gate 192 when all of the outputs of the counter 182 are at logic 0 level. Similarly, the AND gate 194 acts to decouple the enable input 224 of the counter 184 from clocking signals whenever all outputs of counter 184 are at the logic 0 level. In this manner then, the counting of counters 182 and 184 is stopped when the output value of each respective counter reaches zero.

The latch 202 responds to an input signal applied to the input 242 to latch the output of the duration control means 150 and provide the shock control signal on line 144. The input signal at the input 242 will be high when the output of the OR gate 190 is high. Thus, whenever either counter 182 or counter 184 contains a non-zero value, the output of the OR gate 190 Will be high. Responsive to the 32K clock signal on clock line 134 and applied to the input 244 of the latch 202, the duration control means 150 asserts the shock control signal on line 144. As will be discussed in conjunction with FIG. 4, the shock control signal on line 144 is converted to a periodic shock drive signal to control a master switch means to couple the storage capacitor with the cross-point switch in order to deliver cardioverting or defibrillating electrical energy to the heart.

As can be seen, then, the micoprocessor 60 loads a four bit value into the latch 146. The four bit value is then coupled to the counter 182. Similarly, the microprocessor loads a second four bit value into the latch 148. The second four bit value is then coupled to the counter 184. The counters 182 and 184 will count down so long as they each contain a non-zero value and the 2K clock signal on clock line 132 is coupled to enable inputs 210 and 224, respectively. Thus, the four bit value loaded into the counter 182 corresponds to a first time duration, and the four bit value in the counter 184 corresponds to a second time duration. The maximum time duration for both the first and second time durations is 16 cycles of the 2 KHz clock on clock line 132. The latch 202 will assert the shock control signal on line 144 during the first time duration, corresponding to a first cardioverting phase. Further, the latch 202 will assert the shock control signal on line 144 during the second time duration, corresponding to a second cardioverting phase.

The operation of the discharge control logic 130 to generate first and second phase control signals will now be discussed. The phase control means 154 applies a first phase control signal on line 334 and a second phase control signal on line 336. The first phase control signal and the second phase control signal are asserted when they have a logic 1 level, and are deasserted when they have a logic 0 level. The operation of the first and second phase control signals will be discussed further in conjunction with FIG. 3B.

The first phase control signal is asserted when the JK flip flop 272 receives a logic 1 level at the J input 278. The J input 278 will receive a logic 1 level when the output of the AND gate 260 is high, that is, when both inputs to the AND gate 260 are high. This condition will occur when the output 276 of the OR gate 198 is high and when the output 232 of the positive edge detector 158 is high. As discussed above, the output 214 of the positive edge detector 158 will be high in response to a deassertion of the LOCK signal 108 to a logic level 1. The output 276 of the OR gate 198 will be high whenever any of the inputs of the four bit input 204 of the counter 182 is high, that is, whenever the input to the counter 182 is a non-zero, four bit number.

Thus it can be seen that the 32K clock pulse on the clock line 134 which causes the non-zero number to be loaded into the counter 182 also causes the JK flip flop 272 to assert the first phase control signal. In addition, it can be seen that this first assertion of the first phase control signal on line 334 occurs before the first assertion of shock control signal on line 144. The shock control signal on line 144 will be asserted by the latch 202 in response to the 32K clock pulse on the clock line 134 immediately subsequent to the clock pulse on the clock line 134 which causes the JK flip flop 272 to assert the first phase control signal on line 334.

The first phase control signal on line 334 and the shock control signal on line 144 will remain asserted while the counter 182 counts down to zero in response to received pulses coupled from the clock line 132. When the counter 182 reaches a zero value, the latch 202 will deassert the shock control signal on line 144. The edge detect means 152 detects the deassertion of the shock control signal on line 144. When the present state of the shock control signal on line 144 is low and the previous state of the shock control signal, which is latched into the latch 248, is high, the NOR gate 250 will provide at the output 258 a positive pulse. This positive pulse will be of a duration substantially equal to a duration of the 32K clock signal provided on clock line 134 to the input 254 of the latch 248. This positive pulse is coupled through the NAND gate 268 and the inverter 270 to the J input 292 and the K input 290 of the JK flip flop 274. In response, upon receipt of the next 32K clock pulse on clock line 134 to clock input 302, the JK flip flop 274 will provide a second phase control signal to line 336 from its output 282. Thus, the phase control means 152 asserts the second phase control signal on line 336 responsive to the edge detect means 152 detecting the deassertion of the shock control signal on line 144.

The second phase control signal, on line 336, is coupled through the NOR gate 264 to the K input 284 of the JK flip flop 272. In response to the assertion of the second phase control signal, the JK flip flop 272 deasserts the first phase control signal responsive to the 32K clock pulse on the clock line 134 supplied to the clock input 294 of the JK flip flop 272 immediately subsequent to the 32K clock pulse supplied on the clock line 134 to the clock input 302 of the JK flip flop 274 which caused the JK flip flop 274 to assert the second phase control signal on line 336. Thus, the phase control means 154 deasserts the first phase control signal on line 334 responsive to asserting the second phase control signal on line 336.

The inverting output 300 of the JK flip flop 272 is coupled to the input 306 of the positive edge detector 156. When the first phase control signal on line 334 is deasserted, a positive edge results at the inverting output 300 of the JK flip flop 272. The positive edge detector 156 detects this positive edge, and provides a positive pulse at the output 311. This positive pulse indicates that the first phase control signal on line 324 and the second phase control signal on line 326 have switched and the second cardioverting phase may begin. The positive pulse at the output 311 will not be coupled to the load input 226 of the counter 184 unless the second phase control signal 336 is in a logic 1 state, enabling NAND gate 164. The pulse at the output 311 is inverted by the NAND gate 164 and cause the counter 184 to load the four bits of data corresponding to the second time duration into the counter 184. If the data corresponding to the second time duration is non-zero, the output 240 of the OR gate 188 will assume a high state, coupling clocking signals from the output 232 of the positive edge detector 160 to the enable input 224, and causing the shock control signal on line 144 to assume a high logic level. Thus, the duration control means 154 asserts the shock control signal on line 144 responsive to assertion of the second phase control signal on line 336.

When the counter 184 counts to a zero value, the latch 202 deasserts the shock control signal on line 144. The edge detect means 152 detects the deassertion of the shock control signal on line 144 and generates a pulse at the output 258 of the NOR gate 250. This pulse is coupled through the NAND gate 268 and the inverter 270 to the J input 292 of the JK flip flop 274, causing the JK flip flop 274 to reset to a logic 0 level the second phase control signal on line 336 at the output 282. Thus, the phase control means 154 deasserts the second phase control signal on line 336 responsive to the edge detect means 152 detecting the deassertion of the shock control signal on line 144.

The duration control means 150 includes a NOR gate 200. In the event cardioverting or defibrillating electrical energy is to be applied to the heart with a monophasic wave form, the microprocessor 60 loads a zero value into the latch 148. The zero value latched into the latch 148 will cause the output 280 of the NOR gate 200 to remain at a logic 1 level. The logic one level at the output 280 will allow the high level of the output 258 of the NOR gate 250 to be coupled to the $\overline{K}$ input 284 of the JK flip flop 272 through NOR gate 264, thus terminating the first cardioverting phase. The high logic level on the output 280 of the NOR gate 200 will prevent the positive pulse from the output 258 of the NOR gate 250 of the edge detect means 152 from being coupled to the JK flip flop 274 through NAND gate 288. Thus, only the first cardioverting phase will be applied. The second cardioverting phase will be preempted by the zero value loaded into the latch 148.

Figure 3B:
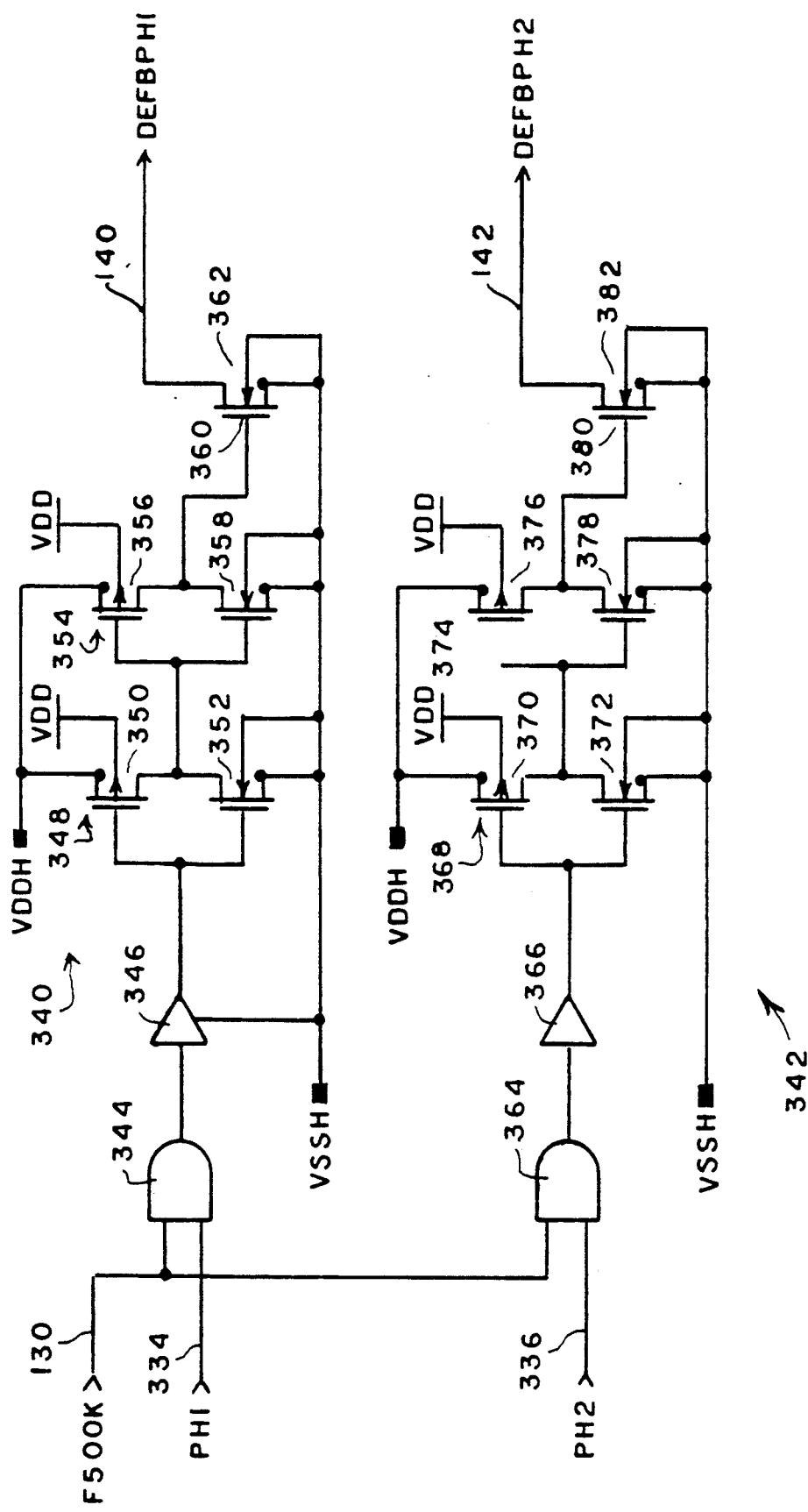

FIG. 3B is a schematic diagram of another portion of the discharge logic circuit 122 of FIG. 2. As previously described, during the first phase of the cardioversion or defibrillation, the first phase control signal on line 334 is a constant high level and the second phase control signal on line 336 is a constant low signal. When the first phase control signal is asserted, the output 140 of the discharge control logic circuit 122 provides the periodic phase one drive control signal. During the second phase, when the second phase control signal on line 336 is a constant high level and the first phase control signal on line 334 is a constant low level, output 142 provides the periodic phase two control drive signal. FIG. 3B shows a first conversion circuit 340 for converting the constant high level first phase control signal on line 334 to a periodic phase one drive control signal on line 140, and a second conversion circuit 342 for converting the constant high level second phase control signal on line 336 to the periodic phase two drive control signal on line 142.

The first conversion circuit 340 includes an AND gate 344. The AND gate 344 has a first input coupled to clock line 130 and a second input coupled to the first phase control signal on line 334. The clock signal on clock line 130 is generated by the clock generating circuit 124 (FIG. 2) and preferably is a 50% duty cycle periodic waveform with a frequency of 500 KHz. The output of the AND gate 344 is coupled through a buffer 346 to a first inverter 348. The first inverter 348 includes a P-channel field effect transistor 350 and an N-channel field effect transistor 352. The output of inverter 348 is coupled to the input of a second inverter 354. The inverter 354 includes a P-channel field effect transistor 356 and an N-channel field effect transistor 358. The output of the second inverter 358 is coupled to the gate 360 of an N-channel field effect transistor 362. The drain of the N-channel field effect transistor 362 supplies the periodic phase one drive control signal on line 140, supplied to the crosspoint switch circuit 128 (FIG. 2).

The second conversion circuit 342 includes an AND gate 364 The AND gate 364 has a first input coupled to the clock signal on clock line 130 and a second input coupled to the second phase control signal on line 336. The output of the AND gate 364 is coupled through a buffer 366 to an inverter 368. The inverter 368 includes a P-channel field effect transistor 370 and an N-channel field effect transistor 372. The output of the inverter 368 is coupled to the input of a second inverter 374. The inverter 374 includes a P-channel field effect transistor 376 and an N-channel field effect transistor 378. The output of the inverter 374 is coupled to the gate 380 of an N-channel field effect transistor 382. The drain of the N-channel field effect transistor 382 is coupled to the periodic phase two drive control signal on line 142, supplied to the crosspoint switch 128.

As can be seen, during the first cardioverting phase, when the first phase control circuit on line 334 is at a constant high level and the second phase control signal on line 336 is at a constant low level, the periodic signal on the clock line 130 is coupled through the AND gate 344 and converted by the first conversion circuit 340 to the periodic phase one drive control signal on line 140. Similarly, during the second cardioverting phase, when the first phase control signal on line 334 is at a constant low level and the second phase control signal on line 336 is at a constant high level, the periodic clock signal on clock line 130 is coupled through the AND gate 364 and converted through the second conversion circuit 342 to the periodic phase two drive control signal on line 142.

Figure 4:
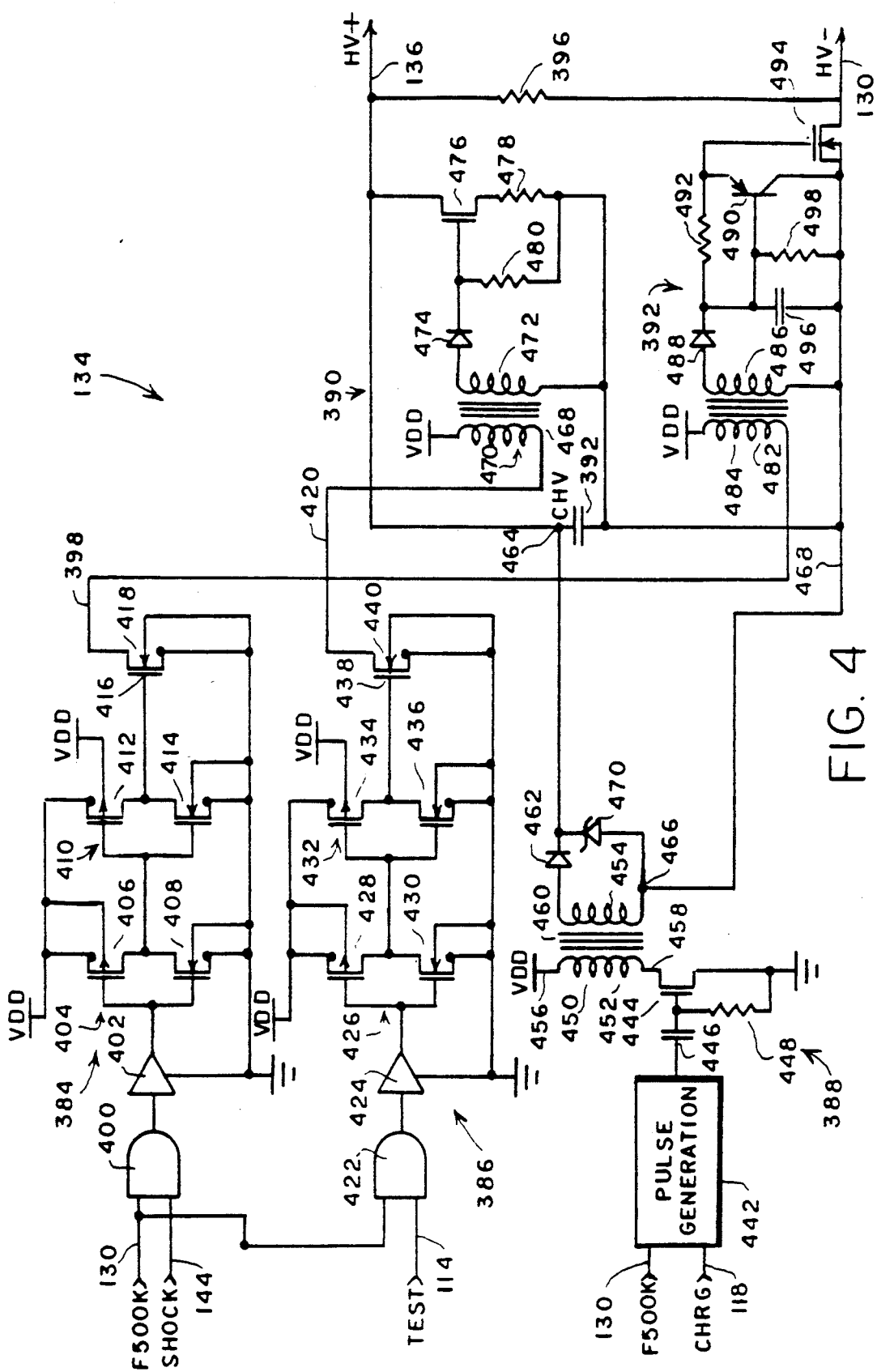
FIG. 4 is a schematic diagram of the high voltage charge and dump circuit of the pulse generator of FIG. 2 embodying additional aspects of the present invention.

Referring now to FIG. 4, it shows a schematic diagram of the high voltage charge and dump circuit 126 of FIG. 2. The high voltage charge and dump circuit 126 generally includes a shock conversion circuit 384, a test conversion circuit 386, a charging circuit 388, a test switch 390, an enable switch 392, the storage capacitor 392 and a resistor 396.

The shock conversion circuit 384 converts the constant high level of the shock control signal received on line 144 from the discharge control logic 122 (FIG. 3A) to a periodic shock drive control signal on line 398. The shock conversion circuit 384 includes an AND gate 400. The AND gate 400 has a first input coupled to the clock signal on clock line 130 and a second input coupled to the shock control signal on line 144. The output of the AND gate 400 is coupled through a buffer 402 to an inverter 404. The inverter 404 includes a P-channel field effect transistor 406 and an N-channel field effect transistor 408. The output of the inverter 404 is coupled to the input of a second inverter 410. The inverter 410 includes a P-channel field effect transistor 412 and an N-channel field effect transistor 414. The output of the inverter 410 is coupled to the gate 416 of an N-channel field effect transistor 418. The drain of the N-channel field effect transistor 418 is coupled to the enable switch 392 by line 398.

The test conversion circuit 386 converts a constant high level of the test signal on control line 114 to a periodic test drive control signal on line 420. The test conversion circuit 386 includes an AND gate 422. The AND gate has a first input coupled to the clock signal on clock line 130 and a second input coupled to the test control signal on line 114, supplied by the microprocessor 60 (FIG. 2). The output of the AND gate 422 is coupled through a buffer 424 to the input of an inverter 426. The inverter 426 includes a P-channel field effect transistor 428 and an N-channel field effect transistor 30. The output of the inverter 426 is coupled to the input of a second inverter 432. The inverter 432 includes a P-channel field effect transistor 434 and a N-channel field effect transistor 436. The output of the inverter 432 is coupled to the gate 438 of an N-channel field effect transistor 440. The drain of the N-channel field effect transistor 440 is coupled to the test switch 390 by line 420.

The charging circuit 388, responsive to receiving the charge control signal over control line 118 (FIG. 2) converts the low voltage of the battery 67 (FIG. 1) to a low duty cycle pulsating high voltage for storing the high voltage electrical energy in the storage capacitor 392. To that end, the charging circuit includes a pulse generation circuit 442. The pulse generation circuit 442 preferably functions in a manner as disclosed in the aforementioned application Ser. No. 07/902,998. The charging circuit 388 further includes an N-channel field effect transistor 444 having a gate coupled to the pulse generation circuit 428 through a capacitor 446. A resistor 448 is coupled across the gate and source of the N-channel field effect transistor 444. The drain of the N-channel field effect transistor 444 is coupled to a flyback transformer 450 having a primary 452 and a secondary 454. The primary 452 includes a first terminal 456 coupled to the battery voltage and a second terminal 458 coupled to the drain of the N-channel field effect transistor 444. The secondary includes a first terminal 460 coupled through a rectifying means such as diode 462 to the positive terminal 464 of the storage capacitor 392, and a second terminal 466 coupled to the negative terminal 468 of the storage capacitor 392. A zener diode 470 is coupled between the positive terminal 464 and the negative terminal 468 of the storage capacitor 392.

The pulse generation circuit 442 applies a periodic voltage to the gate of the N-channel field effect transistor 444, which induces a periodic voltage across the transformer secondary 454 which is rectified by the diode 462 and applied to the capacitor 392 for charging the capacitor 392 and storing the cardioverting or defibrillating electrical energy therein. This charging of the capacitor 392 causes the voltage on the capacitor 392 to increase. The final charge voltage of the capacitor may be on the order of 300 volts.

The periodic test drive control signal on line 420 is coupled to one end of a primary winding 468 of a coupling transformer 470. The other end of the primary winding 468 is coupled to battery potential (VDD). The secondary winding 472 of the coupling transformer 470 has a first end coupled through a rectifying means such as diode 474 to the gate of an N-channel field effect transistor 476. The other end of the secondary winding 472 is coupled to the negative terminal 468 of storage capacitor 392. The drain of the N-channel field effect transistor 476 is coupled to the positive terminal 464 of the storage capacitor 392. The source of the N-channel field effect transistor 476 is coupled through resistor 478 to the negative terminal 468 of the storage capacitor 392. The gate of the N-channel field effect transistor 476 is coupled through a resistor 480 to the negative terminal 468 of the storage capacitor 392.

The periodic enable drive control signal on line 398 is coupled to a first end of a primary winding 482 of a coupling transformer 484. The other end of the primary winding 482 is coupled to battery potential (VDD). The secondary winding 486 of the coupling transformer 484 has a first end coupled through rectifying means such as diode 488 to the base of a PNP transistor 490. The collector of the PNP transistor 490 is coupled to the negative terminal 468 of the storage capacitor 392. The emitter of the PNP transistor 490 is coupled through resistor 492 to the base of the PNP transistor 490 and to the gate of an N-channel field effect transistor 494. A capacitor 496 and a resistor 498 are coupled between the base and the collector of the PNP transistor 490 The source of the N-channel field effect transistor 494 is coupled to the negative terminal 468 of the storage capacitor 392.

The drain of the N-channel field effect transistor 482 is coupled to the output 138. The positive terminal 464 of the storage capacitor 392 is coupled to the output 136.

When the charging of the storage capacitor 392 is completed, the microprocessor 60 provides either a test control signal over line 114 or activates the discharge control circuit 122 as discussed above in relation to FIG. 3A. The test control signal 114 ultimately results in all of the electrical energy stored in the storage capacitor 392 being discharged internally within the high voltage charge and test circuit 126 in a manner to be described hereinafter. Alternatively, the discharge control logic circuit may supply a shock control signal on line 144 which ultimately results in the capacitor 392 being coupled to the crosspoint switch 128 of FIG. 2, as described hereinafter, to enable the cardioverting or defibrillating electrical energy stored in storage capacitor 392 to be applied to electrodes 46 and 44 of lead 36 for cardioverting or defibrillating the atria of the heart.

The test control signal on line 114 and the shock control signal on line 144 are steady state constant level control signals. The shock conversion circuit 384, responsive to receiving the steady state shock control signal on line 144, couples the clock signal on clock line 130 through AND gate 400 to convert the steady state shock control signal to a periodic shock drive control signal on line 398. Similarly, the test conversion circuit 386, responsive to receiving the steady state test signal on line 114, couples the clock signal on clock line 130 through AND gate 422 to convert the steady state test signal on line 114 to the periodic test drive control signal on line 420.

The periodic test drive control signal on line 420 provides a periodic voltage across the primary 468 of the coupling transformer 470. This in turn induces a voltage across the secondary 472 of the coupling transformer 470. The diode 474 rectifies the periodic test drive control signal coupled across transformer 470 to turn transistor 476 on. As a result, when the transistor 476 is turned on, the electrical energy stored in the capacitor 392 is discharged through transistor 476 internally within the high voltage charge and test circuit 126. The resistor 480 turns the transistor 476 off when the test control signal is terminated. Thus, the transistor 476 acts as a test switch.

Similarly, the periodic shock drive control signal on line 398 provides a periodic voltage across the primary 482 of the coupling transistor 484. This in turn induces a periodic enable control signal across the secondary 486 of the coupling transformer 484. The diode 488 rectifies the periodic shock drive control signal coupled across transformer 484 to charge capacitor 496 and turn transistor 494 on. As will be noted in the figure, the transistor 494 is coupled in series with the negative terminal 468 of the capacitor 380. As a result, when the transistor 494 is turned on by the periodic shock drive control signal, the capacitor 392 is coupled across outputs 142 and 144 of the high voltage charge and test circuit 126 for coupling the capacitor 392 to the crosspoint switch circuit 128 of FIG. 2. The transistor 494 thus acts as a master switch means for selectively decoupling the storage capacitor from the lead means. The PNP transistor 490, coupled between the gate and source of the N-channel field effect transistor 494, acts as an emitter follower to rapidly turn off transistor 494 when the periodic shock drive control signal is deasserted.

Figure 5:
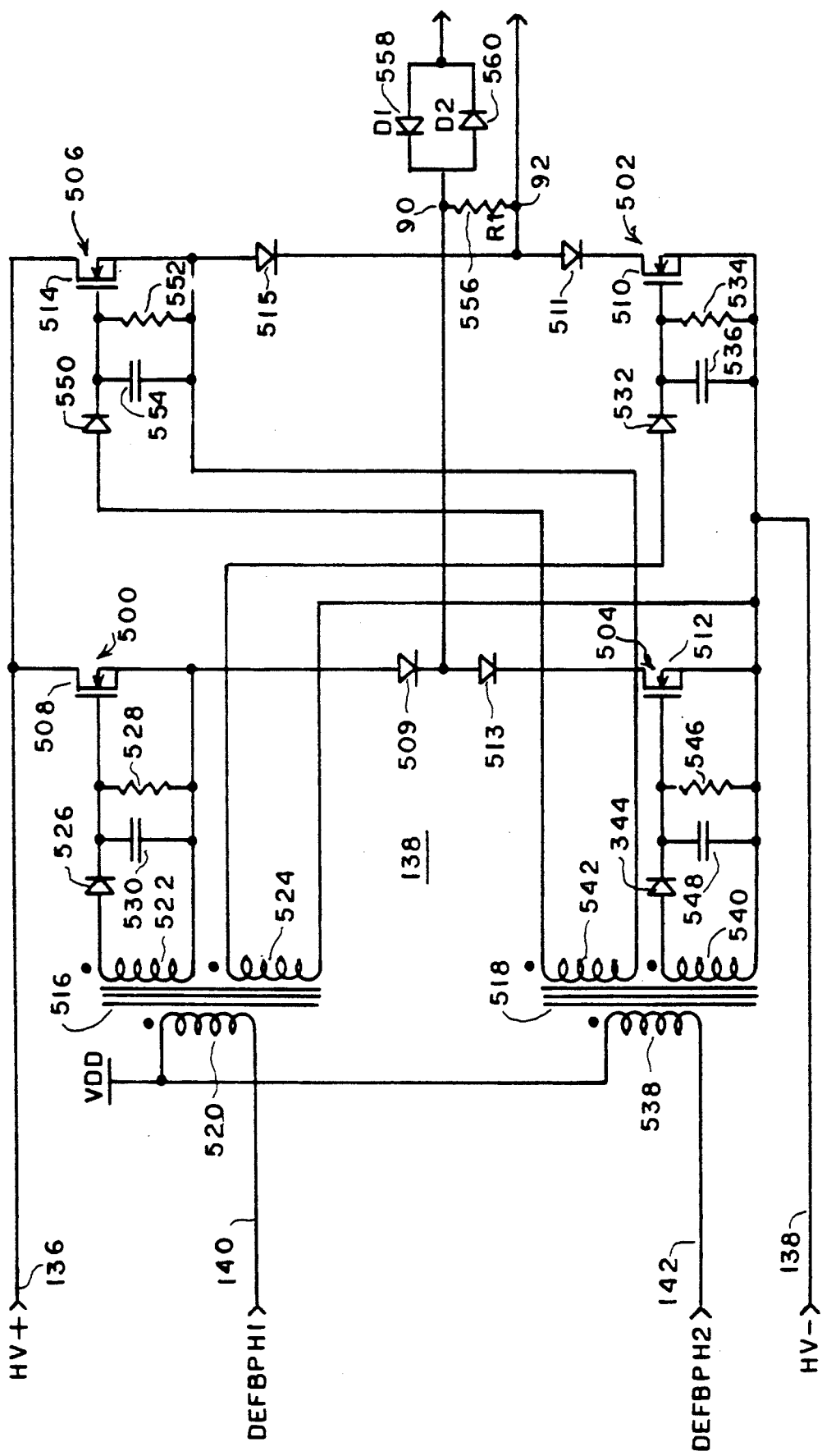
FIG. 5 is a schematic diagram of the crosspoint switch circuit of the pulse generator of FIG. 2 embodying further aspects of the present invention.

Referring now to FIG. 5, it illustrates, in schematic circuit diagram form, the high voltage crosspoint switch circuit 128 illustrated in FIG. 2. The crosspoint switch circuit 128 generally includes a first switch 500, a second switch 502, a third switch 504, and a fourth switch 506. The switches 500, 502, 504, and 506 preferably take the form of N-channel field-effect transistors 508, 510, 512, and 514 respectively. The high voltage crosspoint switch circuit 128 further includes a first isolation or coupling transformer 516 and a second isolation or coupling transformer 518.

The drains of transistors 508 and 514 are coupled to the output 136 of the high voltage charge and dump circuit 126. The sources of transistors 510 and 512 are coupled to the output 138 of the high voltage charge and test circuit 126. The source of transistor 508 and the drain of transistor 512 are coupled to the output 90 of the high voltage crosspoint switch circuit 128. The source of transistor 514 and the drain of transistor 510 are coupled to the output 92 of the high voltage crosspoint switch circuit 138. As a result, when the enable switch transistor 494 of the high voltage charge and test circuit 126 (FIG. 4) is turned on, transistor 512 is coupled between the negative terminal 468 of capacitor 392 and output 90 and transistor 510 is coupled between the negative terminal 468 of capacitor 392 and output 92. Transistor 514 is coupled between the positive terminal 464 of capacitor 392 and output 92 and transistor 508 is coupled between the positive terminal 464 of capacitor 392 and output 90.

Diodes 509 and 513 couple transistors 508 and 512, respectively to output 90. Diodes 511 and 515 couple transistors 510 and 514, espectively, to output 92. These diodes block voltages applied externally to the implantable atrial defibrillator 30 from damaging the circuitry of the defibrillator, for example in the event of external defibrillation of the patient.

The first coupling transformer 516 couples the periodic phase one drive control signal to transistors 508 and 510. To that end, coupling transformer 516 includes a primary 520 having a first end coupled to the battery voltage (VDD) and a second end coupled to output 140 of the discharge control logic circuit 122 for receiving the periodic phase one drive control signal. The coupling transformer 516 also includes a pair of secondary windings including a first secondary winding 522 and second secondary winding 524. The first secondary winding includes a first end or terminal which is coupled to the gate of transistor 508 through a rectifying means or diode 526. The second end or terminal of winding 522 is coupled to the source of transistor 508. The gate and source of transistor 508 are coupled together by a resistor 528 and a capacitor 530.

The second secondary winding 524 includes a first end or terminal which is coupled to the gate of transistor 510 by another rectifying means or diode 532. The second end or terminal of secondary winding 524 is coupled to the source of transistor 510. The gate and source of transistor 510 are coupled together by a resistor 534 and a capacitor 536.

The second coupling transformer 518 couples the periodic phase two drive control signal to transistors 512 and 514. To that end, the second coupling transformer 518 includes a primary 538 having a first end or terminal coupled to battery voltage (VDD) and a second end or terminal coupled to the output 142 of the discharge control logic circuit 122. The second coupling transformer 518 further includes a first secondary winding 540 and a second secondary winding 542. The first secondary winding 540 has a first end which is coupled to the gate of transistor 512 by another rectifying means or diode 544. The second end or terminal of winding 540 is coupled to the source of transistor 512. The gate and source of transistor 512 are coupled together by a resistor 546 and a capacitor 548.

The second secondary winding 542 includes a first end or terminal which is coupled to the gate of transistor 514 by another rectifying means or diode 550. The second end of winding 542 is coupled to the source of transistor 514. The gate and source of transistor 514 are coupled together by a resistor 552 and a capacitor 554.

As will be further noted in FIG. 5, a resistor 556 is coupled across outputs 90 and 92 of the high voltage crosspoint switch circuit 128. Also, a pair of diodes 558 and 560 are coupled in antiparallel relation with the cathode of diode 558 being coupled to the anode of diode 560 and the cathode of diode 560 being coupled to the anode of diode 558. The common junction of the cathode of diode 558 and the anode of diode 560 is coupled to output 90 and the common junction of the anode of diode 558 and the cathode of diode 560 are coupled to electrode 46 of lead 36. The antiparallel diodes 558 and 560 together with resistor 556 eliminate leakage currents to the electrodes 46 and 44 of lead 36. In addition, the diodes 558 and 560 and resistor 556 serve to block low voltages which may be present at the field-effect transistor switches during test operations of the storage capacitor 39 from reaching the electrodes 46 and 44.

During phase one of the cardioversion or defibrillation, the periodic phase one drive control signal is conveyed to the primary 520 of the first coupling transformer 516. The periodic phase one drive control signals are induced across the secondary windings 522 and 524. The diodes 526 and 532 rectify the induced control signals and turn on field-effect transistors 508 and 510. This applies the positive terminal of capacitor 392 to output 90 and the source of transistor 494 (FIG. 4) to output 92. When the shock control signal is asserted by the discharge control circuit 122, transistor 494 is turned on, coupling the negative terminal 468 of capacitor 392 to output 92, and applying cardioverting or defibrillating electrical energy to the heart.

During phase two of the cardioversion or defibrillation, the periodic phase two drive control signal is conveyed to primary 538 of the second coupling transformer 518. The periodic phase two drive control signal is thus induced across the secondary windings 540 and 542 of the second coupling transformer 518. The diodes 544 and 550 rectify the phase two drive control signals to turn on transistors 512 and 514. As a result, the positive terminal of the capacitor 392 is coupled to output 92. When the shock control signal is asserted by the discharge control circuit 122, transistor 494 is turned on, coupling the negative terminal 468 of Capacitor 392 to output 90. Resistors 528 and 534 turn transistors 508 and 510 off when the phase one drive control signal is terminated and resistors 546 and 552 turn off transistors 512 and 514 when the phase two drive control signal is terminated.

As will be noted from the foregoing, transformer coupling of the control signals is utilized for the enable control signal, the test control signal, the phase one control signal, and the phase two control signal. Such transformer coupling together with the rectifying diodes for turning respective field-effect transistor switches on and off are preferably utilized to reduce parts count in the resulting atrial defibrillator. The foregoing hence reduces circuitry complexity with the resulting advantage of high reliability.

In operation, and making reference to FIGS. 1 through 5, sense amplifiers 50 and 54 and R wave detectors 52 and 56 continuously detect for electrical activations (R waves) of the heart 10. When the intervals between the R waves determined by the microprocessor 60 indicate that atrial fibrillation may be present, the microprocessor 60 activates sense amplifier 58. Atrial activity of the heart 10 is then monitored. If the microprocessor 60 determines that atrial fibrillation is present, it issues the charge control signal on line 118 to cause the high voltage charge and test circuit 126 to charge the storage capacitor 392 (FIG. 4). The capacitor 392 is slowly charged and will achieve a full charge of, for example, 300 volts, in about one minute.

Figure 6:
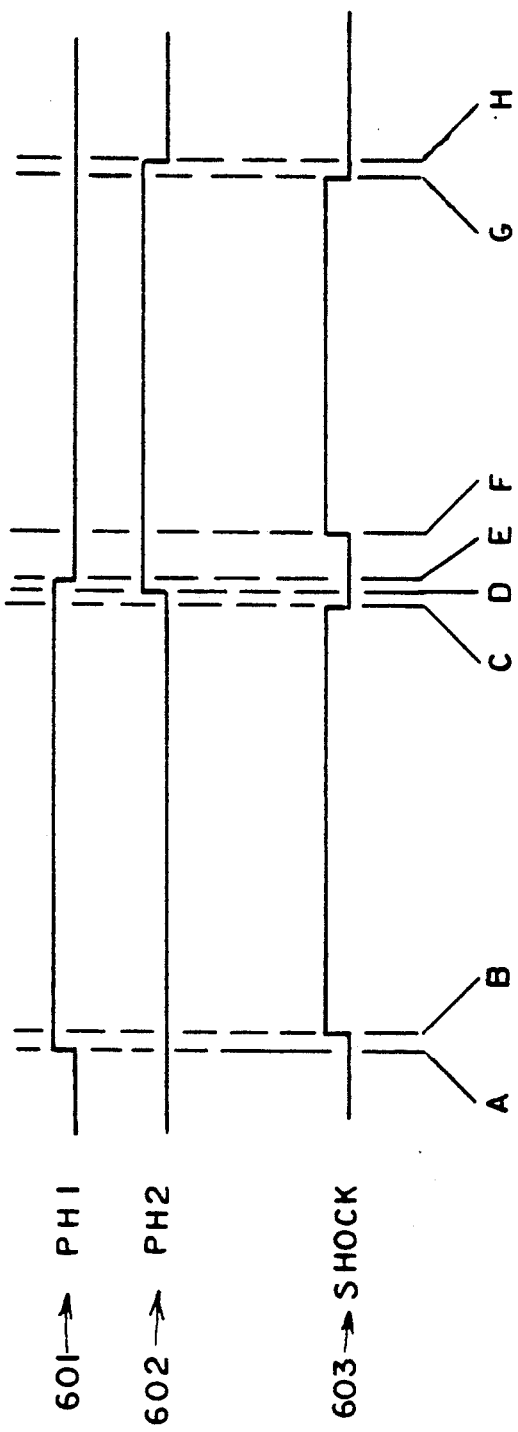
FIG. 6 is a timing diagram showing selected signals of the discharge logic circuit of FIG. 3.

Making further reference to FIG. 6, it shows a timing diagram showing selected signals of the discharge logic circuit of FIG. 3. FIG. 6 shows a waveform 601 for the first phase control signal on line 334 (FIG. 3A), waveform 602 for the second phase control signal on line 336, and waveform 603 for the shock control signal on line 144.

When the charging of the storage capacitor 392 is completed, the microprocessor 60 activates the discharge control circuit 122. The microprocessor 60 initially holds a discharge disable signal on LOCK line 108. The microprocessor 60 then provides over the data bus 120 to latches 146 and 148 (FIG. 3A) four-bit values corresponding to the duration of the first and second cardioverting phases. The microprocessor latches the four-bit values by asserting control signals HVPH1WD and HVPH2WD on lines 112 and 114, respectively.

At time A (FIG. 6), in response to the removal of the LOCK signal 108, the discharge logic circuit 122 generates a first phase control signal having a constant level and converts that signal to a periodic phase one drive control signal. The periodic phase one drive control signal causes the high voltage crosspoint switch 128 to couple the positive terminal of the storage capacitor to output 90 and to couple the source of transistor 494 to output 92.

Subsequent to generating the first phase control signal, the discharge control circuit 122 generates a shock control signal having a constant level. The high voltage charge and dump circuit 126 converts that signal to a periodic shock control signal. The periodic shock control signal turns on transistor 494 and couples the storage capacitor 392 to the lead means. When counter 182 counts down to zero, the shock control signal is deasserted, at time C, the transistor 494 is turned off, and the storage capacitor 392 is decoupled from the output 92.

In response to the deassertion of the shock control signal, the discharge control circuit 122 asserts the second phase control signal, at time D. The second phase control signal, having a constant level, is converted to a periodic phase two control signal. Responsive to assertion of the second phase control signal, the discharge control logic deasserts the first phase control signal, at time E. Thus, the positive terminal 464 of the storage capacitor 392 is decoupled from output 90 and coupled to output 92, and the source of transistor 494 is decoupled from output 92 and coupled to output 90.

Responsive to the deassertion of the first phase control signal, the discharge control circuit 122 asserts the shock control signal at time F, beginning the second cardioverting phase. When the counter 184 counts down to zero, the shock control signal is deasserted, at time G, ending the second cardioverting phase. Responsive to the deassertion of the shock control signal, the second phase control signal is deasserted, at time H.

Upon completion of phase two, the sense amplifiers 50 and 54 and the R wave detectors 52 and 56 once again monitor electrical activations (R waves) of the heart to enable the microprocessor to determine if the atrial fibrillation has been arrested. If atrial fibrillation should persist, the foregoing operation is repeated.

As can be seen from the foregoing, the present invention provides a defibrillator having a crosspoint switch and master switch which decouples the storage capacitor from the lead means while the crosspoint switch connections are changed. The present invention further provides independent control of both the first and the second cardioverting phase.

While a particular embodiment of the present invention has been shown and described, modifications may be made, and it is therefore intended to cover in the appended claims all such changes and modifications which fall within the true spirit and scope of the invention.

What is claimed is:

1. A pulse generator for use in a defibrillator for providing cardioverting electrical energy to the heart through lead means, said pulse generator including a storage capacitor having a positive terminal and a negative terminal for providing said cardioverting electrical energy, and charging means for charging said storage capacitor, the improvement comprising:
coupling means for selectively coupling said storage capacitor to said lead means with a first polarity for applying a first portion of said cardioverting electrical energy through said lead means to the heart during a first cardioverting phase, and with a second polarity reversed from said first polarity for applying a second portion of said cardioverting electrical energy through said lead means to the heart during a second cardioverting phase; and
master switch means for selectively decoupling said storage capacitor from said lead means between said first and second cardioverting phases.

2. A pulse generator as defined in claim 1 wherein said coupling means includes a crosspoint switch for selectively coupling said storage capacitor to said lead means.

3. A pulse generator as defined in claim 2 wherein said master switch means is coupled between said storage capacitor and said crosspoint switch.

4. A pulse generator as defined in claim 2 wherein said master switch means is coupled between said crosspoint switch and said lead means.

5. A pulse generator as defined in claim 2 wherein said lead means comprise first and second electrodes and wherein said crosspoint switch includes a first switch means for selectively coupling said positive terminal to said first electrode, a second switch means for selectively coupling said negative terminal to said second electrode, a third switch means for selectively coupling said positive terminal to said second electrode, and a fourth switch means for selectively coupling said negative terminal to said first electrode.

6. A pulse generator as defined in claim 5 wherein said first switch means couples said positive terminal to said first electrode and said second switch means couples said negative terminal to said second electrode during said first cardioverting phase, and said third switch means couples said positive terminal to said second electrode and s id fourth switch means couples said negative terminal to said first electrode during said second cardioverting phase.

7. A pulse generator as defined in claim 6 wherein said master switch means decouples said storage capacitor from said lead means before said third switch means couples said positive terminal to said second electrode and said fourth switch means couples said negative terminal to said first electrode.

8. A pulse generator as defined in claim 5 wherein said crosspoint switch is responsive to a first control signal for coupling said storage capacitor to said lead means with said first polarity and responsive to a second control signal for coupling said storage capacitor to said lead means with said second polarity.

9. A pulse generator as defined in claim 8 wherein said first switch means, said second switch means, said third switch means and said fourth switch means each comprise a field effect transistor.

10. A pulse generator as defined in claim 8 further including isolation means for coupling said first control signal to said first and second switch means and for coupling said second control signal to said third and fourth switch means.

11. A pulse generator as defined in claim 10 wherein said isolation means comprises a first transformer including a primary for receiving said first control signal, a first secondary coupled to said first switch means and a second secondary coupled to said second switch means and wherein said isolation means further includes a second transformer including a primary for receiving said second control signal, a first secondary coupled to said third switch means and a second secondary coupled to said fourth switch means.

12. A pulse generator as defined in claim 11 wherein said first and second control signals have time varying waveforms and wherein said coupling means includes first rectifying means coupling said first transformer first secondary to said first switch means, second rectifying means coupling said first transformer second secondary to said second switch means, third rectifying means coupling said second transformer first secondary to said third switch means, and fourth rectifying means coupling said second transformer second secondary to said fourth switch means, said first and second rectifying means rectifying said first control signal and said third and fourth rectifying means rectifying said second control signal.

13. A pulse generator as defined in claim 8 wherein said master switch means is responsive to a shock control signal for decoupling said storage capacitor from said lead means 14. A pulse generator as defined in claim 13 further comprising shock control isolation means for coupling said shock control signal to said master switch means.

15. A pulse generator as defined in claim 8 wherein said master switch means comprises a field effect transistor.

16. A pulse generator as defined in claim 14 wherein said shock control isolation means comprises a transformer including a primary for receiving said shock control signal and a secondary coupled to said master switch means.

17. A pulse generator as defined in claim 16 wherein said shock control signal has a time varying waveform and wherein said master switch means includes shock control rectifying means coupling said transformer secondary to said master switch, said shock control rectifying means rectifying said shock control signal.

18. A pulse generator as defined in claim 1 wherein said first cardioverting phase is of a first time duration and said second cardioverting phase is of a second time duration.

19. A pulse generator as defined in claim 18 further comprising duration control means for controlling said first time duration and said second time duration.

20. A pulse generator as defined in claim 19 wherein said master switch means is responsive to a shock control signal asserted by said duration control means, said first time duration corresponding to a first assertion of said shock control signal and said second time duration corresponding to a second assertion of said shock control signal.

21. A pulse generator as defined in claim 20 wherein said duration control means asserts said shock control signal responsive to a received duration control input.

22. A pulse generator as defined in claim 21 wherein said duration control means comprises a counter.

23. A pulse generator as defined in claim 20 wherein said coupling means is responsive to a first control signal for coupling said storage capacitor to said lead means with said first polarity and responsive to a second control signal for coupling said storage capacitor to said lead means with a second polarity.

24. A pulse generator as defined in claim 23 wherein said first control signal is asserted before said first assertion of said shock control signal.

25. A pulse generator as defined in claim 23 further comprising phase control means for controlling assertion and deassertion of said first control signal and said second control signal.

26. A pulse generator a defined in claim 25 wherein said phase control means asserts said first control signal before said first assertion of said shock control signal.

27. A pulse generator as defined in claim 26 further comprising edge detect means for detecting deassertion of said shock control signal.

28. A pulse generator as defined in claim 27 wherein said edge detect means comprises a latch.

29. A pulse generator as defined in claim 27 wherein said phase control means asserts said second control signal responsive to said edge detect means detecting deassertion of said shock control signal.

30. A pulse generator as defined in claim 29 wherein said phase control means deasserts said first control signal responsive to asserting said second control signal.

31. A pulse generator as defined in claim 30 wherein said duration control means asserts said shock control signal responsive to assertion of said second control signal.

32. A pulse generator as defined in claim 31 wherein said phase control means deasserts said second control signal responsive to said edge detect means detecting deassertion of said shock control signal.

33. A pulse generator as defined in claim 19 wherein said duration control means controls said first and second time durations responsive to a received duration control input.

34. A pulse generator as defined in claim 33 wherein said coupling means is responsive to a first control signal for coupling said storage capacitor to said lead means with said first polarity and responsive to a second control signal for coupling said storage capacitor to said lead means with a second polarity.

35. A pulse generator as defined in claim 34 further comprising phase control means for generating said first and second signals responsive to said duration control means.

36. A pulse generator as defined in claim 35 wherein said duration control means controls said second time duration to be of substantially zero time duration responsive to a particular received duration control input.

37. A pulse generator as defined in claim 36 further comprising disable means responsive to said particular received duration control input for disabling said phase control means.

38. A method for providing electrical energy stored in a storage capacitor having a positive terminal and a negative terminal through lead means having a first electrode and a second electrode for conveying said electrical energy to a heart, the method comprising the steps of:
  applying a first portion of said electrical energy with a first polarity through said lead means to the heart during a first cardioverting phase;
  applying a second portion of said electrical energy with a second polarity through said lead means to the heart during a second cardioverting phase, said second polarity being opposite said first polarity;
  decoupling said lead means from said storage capacitor between said first and second cardioverting phases.

39. A method as defined in claim 38 wherein said first cardioverting phase step includes providing a first control signal for selectively coupling said storage capacitor to said lead means and said second cardioverting phase step includes providing a second control signal for selectively coupling said storage capacitor to said lead means, and wherein said decoupling step includes providing a shock control signal for selectively decoupling said lead means from said storage capacitor.

40. A method as defined in claim 39 wherein said first cardioverting phase step includes asserting said first control signal to couple said positive terminal to said first electrode and said negative terminal to said second electrode and said second cardioverting phase step includes asserting said second control signal to couple said negative terminal to said first electrode and said positive terminal to said second electrode.

41. A method as defined in claim 40 wherein said first cardioverting phase step includes asserting said first control signal and thereafter asserting said shock control signal to couple said lead means to said storage capacitor.

42. A method as defined in claim 40 wherein said decoupling step includes deasserting said shock control signal to decouple said lead means from said storage capacitor.

43. A method as defined in claim 42 wherein said second cardioverting phase step includes asserting said second control signal responsive to deassertion of said shock control signal.

44. A method as defined in claim 40 wherein said second cardioverting phase step includes deasserting said first control signal responsive to asserting said second control signal.

45. A method as defined in claim 44 wherein said second cardioverting phase step includes deasserting sad second control signal responsive to deassertion of said shock control signal.

46. A crosspoint switch control circuit for controlling a crosspoint switch and a master switch for use in a defibrillator for providing cardioverting electrical energy to a heart through lead means having first and second electrodes for providing said cardioverting electrical energy to the heart from a storage capacitor having a positive and a negative terminal, said crosspoint switch being responsive to a first control signal for coupling said positive terminal to said first electrode and said negative terminal to said second electrode and responsive to a second control signal for coupling said positive terminal to said second electrode and said negative terminal to said first electrode, said master switch being responsive to a shock control signal for decoupling said storage capacitor from said lead means, said control circuit comprising:

phase control means coupled to said crosspoint switch for generating said first and second control signals; and duration control means for controlling said phase control means and generating said shock control signal to cause said master switch to decouple said storage capacitor from said lead means between said first and second cardioverting phases.

* * * * *